United States Patent
Slate (10) Patent No.: US 11,690,508 B2
(45) Date of Patent: *Jul. 4, 2023

(54) SYSTEMS AND METHOD FOR PREVENTING AIR ESCAPE AND MAINTAINING AIR DISTENSION

(71) Applicant: Jason Andrew Slate, Miami, FL (US)

(72) Inventor: Jason Andrew Slate, Miami, FL (US)

(*) Notice: Subject to any disclaimer, the term of this patent is extended or adjusted under 35 U.S.C. 154(b) by 127 days.

This patent is subject to a terminal disclaimer.

(21) Appl. No.: 17/167,224

(22) Filed: Feb. 4, 2021

(65) Prior Publication Data

US 2021/0153733 A1 May 27, 2021

Related U.S. Application Data (63) Continuation of application No. 15/678,389, filed on Aug. 16, 2017, now Pat. No. 10,939,814.

(60) Provisional application No. 62/377,248, filed on Aug. 19, 2016.

(51) Int. Cl.
*A61B 1/31* (2006.01)
*A61B 1/00* (2006.01)

(52) U.S. Cl.
CPC ............ *A61B 1/31* (2013.01); *A61B 1/00137* (2013.01); *A61B 1/00154* (2013.01); *A61B 1/00101* (2013.01)

(58) Field of Classification Search
CPC ....... A61B 1/267; A61B 1/2676; A61B 1/273; A61B 1/2733; A61B 1/2736; A61B 1/31; A61B 1/00154; A61B 1/00135; A61B 1/00142; A61M 29/00
See application file for complete search history.

(56) References Cited

U.S. PATENT DOCUMENTS

| | | | | |
|---|---|---|---|---|
| 3,871,358 A * | 3/1975 | Fukuda | ............... | A61B 1/00154 600/585 |
| 4,117,847 A * | 10/1978 | Clayton | ................ | A61F 5/4408 604/179 |
| 4,538,594 A * | 9/1985 | Boebel | ...................... | A61B 1/31 600/105 |
| 4,776,845 A * | 10/1988 | Davis | ....................... | A61B 1/31 600/114 |
| 4,957,486 A * | 9/1990 | Davis | ..................... | A61M 25/01 600/116 |
| 5,779,624 A * | 7/1998 | Chang | ....................... | A61B 1/31 600/114 |
| 5,941,815 A * | 8/1999 | Chang | ....................... | A61B 1/31 600/114 |
| 6,149,581 A * | 11/2000 | Klingenstein | ............ | A61B 1/31 600/114 |
| 6,315,714 B1 * | 11/2001 | Akiba | ................ | A61B 1/00135 604/524 |

(Continued)

*Primary Examiner* — Ryan N Henderson
(74) *Attorney, Agent, or Firm* — Ballard Spahr LLP (57) ABSTRACT

A device for preventing air escape and maintaining colonic air distension can include a body, a distal gasket coupled to a distal end of the body, a proximal gasket coupled to a proximal end of the body, and a diaphragm coupled to the proximal gasket. The distal and proximal gaskets can form a fluid-tight seal with a colonoscope positioned within central bores of the distal gasket, the body, and the proximal gasket, and the diaphragm can conform to and form a fluid-tight seal with at least one of an anus and a stoma of a subject.

20 Claims, 5 Drawing Sheets

(56) References Cited

U.S. PATENT DOCUMENTS

| | | | | |
|---|---|---|---|---|
| 6,503,192 B1* | 1/2003 | Ouchi | A61B 1/00154 | 600/128 |
| 7,537,562 B2* | 5/2009 | Takano | A61B 1/00082 | 600/114 |
| 8,177,755 B2* | 5/2012 | Berry | A61B 17/3462 | 604/167.03 |
| 8,216,159 B1* | 7/2012 | Leiboff | A61B 5/03 | 600/560 |
| 8,419,695 B2* | 4/2013 | Rauker | A61B 1/00082 | 604/277 |
| 9,232,947 B2* | 1/2016 | Brenner | A61B 5/415 | |
| 10,080,481 B2* | 9/2018 | Goldwasser | A61B 1/2736 | |
| 10,463,236 B2* | 11/2019 | Simchony | A61B 1/00149 | |
| 2003/0083546 A1* | 5/2003 | Butler | A61B 1/31 | 600/114 |
| 2003/0229296 A1* | 12/2003 | Ishikawa | A61B 1/00082 | 600/585 |
| 2003/0233025 A1* | 12/2003 | Saadat | A61B 1/00154 | 600/114 |
| 2005/0038335 A1* | 2/2005 | Gross | A61B 1/273 | 600/116 |
| 2005/0059992 A1* | 3/2005 | Leiboff | A61M 31/00 | 606/197 |
| 2005/0159644 A1* | 7/2005 | Takano | A61B 1/00082 | 600/116 |
| 2005/0197531 A1* | 9/2005 | Cabiri | A61B 1/00156 | 600/101 |
| 2005/0261553 A1* | 11/2005 | Swain | A61M 1/777 | 600/156 |
| 2006/0271095 A1* | 11/2006 | Rauker | A61B 1/31 | 606/197 |
| 2007/0135679 A1* | 6/2007 | Hunt | A61B 1/00154 | 600/102 |
| 2007/0213661 A1* | 9/2007 | Gobel | A61F 2/0013 | 604/96.01 |
| 2008/0033244 A1* | 2/2008 | Matsui | A61B 1/01 | 600/114 |
| 2008/0097292 A1* | 4/2008 | Cabiri | A61B 1/00082 | 604/95.01 |
| 2008/0172010 A1* | 7/2008 | Degtiar | A61B 1/00148 | 604/264 |
| 2009/0062614 A1* | 3/2009 | Adzich | A61B 1/31 | 600/129 |
| 2009/0062837 A1* | 3/2009 | Gasche | A61B 1/31 | 600/114 |
| 2009/0124862 A1* | 5/2009 | Cohen | A61B 1/00154 | 600/235 |
| 2009/0131751 A1* | 5/2009 | Spivey | A61B 17/3462 | 600/114 |
| 2009/0171268 A1* | 7/2009 | Williams, Jr. | A61M 13/003 | 604/26 |
| 2009/0203995 A1* | 8/2009 | Matonick | A61M 25/1011 | 600/560 |
| 2010/0063358 A1* | 3/2010 | Kessler | A61B 1/00142 | 600/121 |
| 2010/0069716 A1* | 3/2010 | Chin | A61B 1/0051 | 600/114 |
| 2010/0185056 A1* | 7/2010 | Gordon | A61M 25/0105 | 600/158 |
| 2010/0268162 A1* | 10/2010 | Shelton, IV | A61B 17/3498 | 604/167.01 |
| 2010/0280489 A1* | 11/2010 | Nishtala | A61M 3/0287 | 604/514 |
| 2010/0298775 A1* | 11/2010 | Berry | A61B 17/3462 | 604/167.03 |
| 2010/0331625 A1* | 12/2010 | Rosemurgy | A61B 1/012 | 600/116 |
| 2011/0105850 A1* | 5/2011 | Voegele | A61B 17/3423 | 606/119 |
| 2013/0116559 A1* | 5/2013 | Levin | A61B 8/00 | 604/257 |
| 2013/0225925 A1* | 8/2013 | Kang | A61B 1/00154 | 600/114 |
| 2014/0018625 A1* | 1/2014 | Lal | A61B 1/31 | 600/115 |
| 2014/0107692 A1* | 4/2014 | Matsuo | A61M 29/02 | 606/192 |
| 2014/0128677 A1* | 5/2014 | Lenart | A61B 1/00154 | 600/114 |
| 2014/0336574 A1* | 11/2014 | Simmons | A61M 3/0295 | 604/101.05 |
| 2015/0112129 A1* | 4/2015 | Ozdil | A61B 1/018 | 606/191 |
| 2015/0351617 A1* | 12/2015 | Simchony | A61B 1/00154 | 600/102 |
| 2016/0353980 A1* | 12/2016 | Takahashi | A61B 1/00078 | |
| 2017/0065155 A1* | 3/2017 | Farhadi | A61B 1/00082 | |
| 2017/0224198 A1* | 8/2017 | Yanagihara | A61B 1/0057 | |
| 2018/0049626 A1* | 2/2018 | Slate | A61B 1/00137 | |
| 2018/0263469 A1* | 9/2018 | Okaniwa | G02B 23/24 | |
| 2018/0326165 A1* | 11/2018 | Holbrook | A61M 13/003 | |
| 2020/0037857 A1* | 2/2020 | Newman | A61B 1/31 | |

\* cited by examiner

SYSTEMS AND METHOD FOR PREVENTING AIR ESCAPE AND MAINTAINING AIR DISTENSION

CROSS-REFERENCE TO RELATED APPLICATION

This application is a continuation of U.S. patent application Ser. No. 15/678,389, filed Aug. 16, 2017, which claims priority to and the benefit of the filing date of U.S. Provisional Patent Application No. 62/377,248, filed Aug. 19, 2016. Each of these applications is incorporated herein by reference in its entirety.

FIELD

This disclosure relates to systems and methods for maintaining air distension within the colon or small bowel of a subject.

BACKGROUND

During a colonoscopy, a professional administering the exam can be required to insert an instrument into a patient. Escaped air can cause increased difficulty in performing diagnostic and therapeutic maneuvers, increase risk for colonic injury, and compromise the safety of the patient. Problems often arise when air escapes from the colon due to colonic wall spasm or from an incompetent anal sphincter, with resulting colonic wall collapse from deflation. The interface between anus and the inserted instrument can impact the ability of air to distend the colon during the colonoscopy, especially in cases of an incompetent anal sphincter. In cases of procedures involving ostomies or ileostomies, there is no anal sphincter to create this relative seal. Maintaining colonic and small bowel air distension can be critical to ensuring safe resection of lesions and safe treatment of active gastrointestinal bleeding and to aiding in diagnosis. Additionally, failure to maintain colonic air distension can necessitate the repeating of procedures in order to achieve desired results.

SUMMARY

Described herein are devices, systems, and methods for preventing air escape and maintaining air distension in the colon or small bowel of a subject. The device can include a body having a longitudinal axis, an inner surface, an outer surface, a proximal end, and an opposed distal end. The opposed distal end can be spaced from the proximal end relative to the longitudinal axis. The inner surface of the body can define a central bore. The central bore can surround the longitudinal axis and extend from the proximal end to the distal end of the body. The central bore can also have a diameter. The device can also include a distal gasket coupled to the distal end of the body. The distal gasket can define a central bore and have a central axis that is aligned with the longitudinal axis of the body. The central bore of the distal gasket can have a diameter that is less than the diameter of the central bore of the body. The device can also include a proximal gasket coupled to the proximal end of the body. The proximal gasket can define a central bore and have a central axis that passes through the central bore and is aligned with the longitudinal axis of the body (such that the gasket circumferentially surrounds the central bore and the portion of the central axis passing through the bore). In exemplary aspects, the proximal gasket can extend radially outwardly relative to the central axis (and the longitudinal axis of the body). Optionally, the proximal gasket can be oriented generally perpendicularly relative to the central axis (and the longitudinal axis of the body). The central bore of the proximal gasket can have a diameter that is less than the diameter of the central bore of the body. The device can further include a diaphragm coupled to the proximal gasket. The diaphragm can extend radially outwardly from the proximal gasket relative to the central axis of the proximal gasket and the longitudinal axis of the body. The distal and proximal gaskets can be configured to form a fluid-tight seal with a colonoscope positioned within the central bores of the distal gasket, the body, and the proximal gasket. The diaphragm can be shaped to conform to an anus of a subject.

Further disclosed is a method for preventing air escape and maintaining air distension in the colon. The method can include advancing a colonoscope through at least one of an anus and a stoma of a subject. The method can also include advancing the disclosed device in a proximal direction over the colonoscope such that portions of the colonoscope pass through the central bores of the proximal gasket, the body, and the distal gasket of a device as disclosed herein. A distal end of the colonoscope can protrude from the distal gasket (in a distal direction), and the distal and proximal gaskets can form a fluid-tight seal with the colonoscope. The method can further include positioning the diaphragm of the device in contact with at least one of the anus and the stoma of the subject. In this aspect, the device can be advanced proximally over the colonoscope to a desired use position in which the diaphragm of the device can form a fluid-tight seal with at least one of the anus and the stoma of the subject. In use, the disclosed device can slide relative to the colonoscope (and the body of the subject) as needed to selectively seal air within the subject and to selectively release air from the subject. Thus, this process can be instantaneously and selectively reversed by sliding the device away (in a distal direction) 1-2 mm to allow for an immediate release of air from the subject. Conversely, the device can also be readily available by a sliding movement (in a proximal direction) to return to the subject's orifice to provide the benefit of maintaining the air within the lumen temporarily and therefore achieving procedural goals, intermittently throughout the procedure. Although selective sliding movement of the device is possible, it is also contemplated that the device can remain static when in contact with the anus or the stoma of the subject, with minor adjustments of the position of the colonoscope being the only movement/adjustment required during the procedure.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE FIGURES

These and other features of the preferred embodiments of the invention will become more apparent in the detailed description in which reference is made to the appended drawings wherein.

DETAILED DESCRIPTION

The present disclosure can be understood more readily by reference to the following detailed description, examples, drawings, and claims, and their previous and following description. However, before the present devices, systems, and/or methods are disclosed and described, it is to be understood that this disclosure is not limited to the specific devices, systems, and/or methods disclosed unless otherwise specified, as such can, of course, vary. It is also to be understood that the terminology used herein is for the purpose of describing particular aspects only and is not intended to be limiting.

The following description is provided as an enabling teaching of the disclosed articles, systems, and methods in their best, currently known embodiments. To this end, those skilled in the relevant art will recognize and appreciate that many changes can be made to the various aspects of the articles, systems, and methods described herein, while still obtaining the beneficial results of the disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to "a gasket" can include two or more such gaskets unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

The term "fluid-tight seal" as used herein refers to seals that prevent passage of gases, liquids, or combinations thereof. As used herein, the term "fluid-tight seal" includes releasable fluid-tight engagement between components such that components can be sealingly connected or engaged when operatively assembled or positioned and then selectively separated and reattached.

As used herein, the term "proximal" refers to a direction toward (or closest to) the subject or patient, whereas the term "distal" refers to a direction away from (or farthest from) the subject or patient. When the terms "proximal" or "distal" are used herein to describe components of a device or system, it is understood that those terms refer to the preferred orientation and positioning of the components when the components are used in their normal and intended way, as further disclosed herein.

Disclosed herein are devices, systems, and methods for preventing air escape and maintaining colonic air distension within a subject or patient. In exemplary applications, it is contemplated that the disclosed devices and systems can be used to maintain colonic air distension within a human patient. However, it is contemplated that the disclosed devices and systems can be used to maintain colonic air distension in other subjects, including for example and without limitation, laboratory animal subjects. In use, it is contemplated that the disclosed devices, systems, and methods can form a seal with the anus of a subject to prevent undesired escape of fluids during a colonoscopy procedure. Although described herein as being used during a colonoscopy procedure, it is contemplated that the disclosed devices and systems can be used in other procedures where a fluid-tight seal with an outer orifice of the body of a subject or patient is desired.

Figure 1:
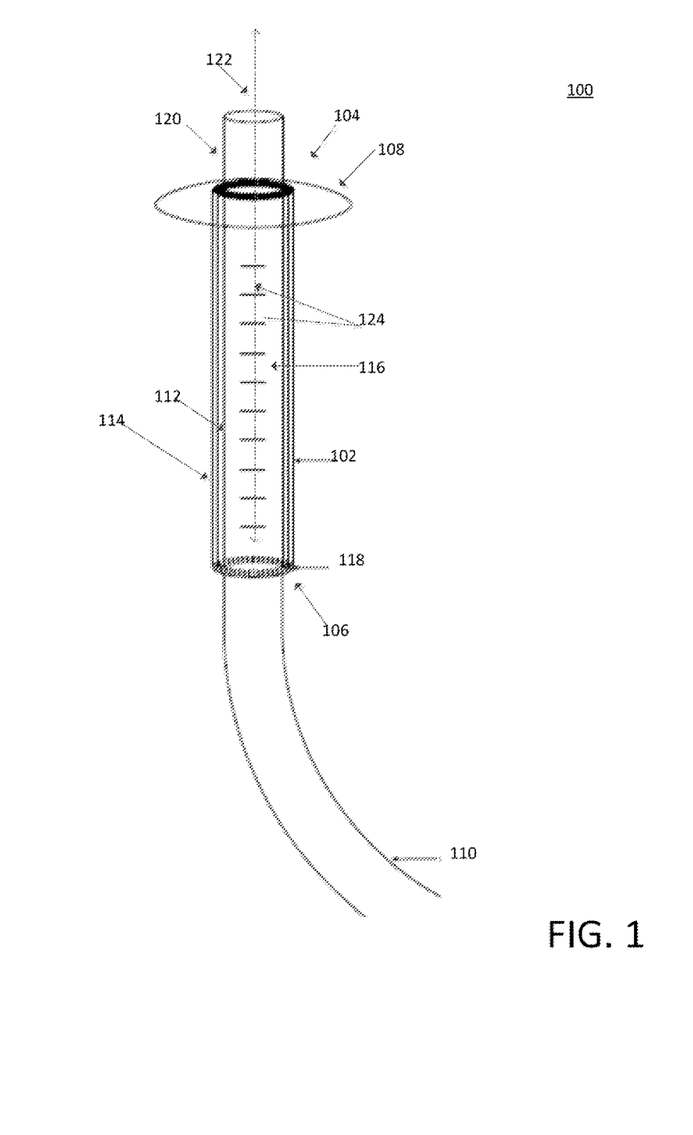
FIG. 1 is a partially transparent side perspective view of an exemplary system for maintaining air distension as disclosed herein.
Figure 2A:
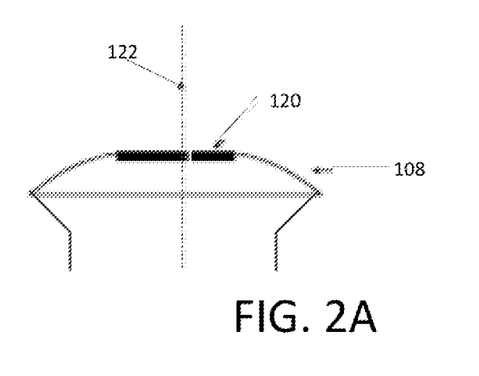
FIG. 2A is a side view of an exemplary diaphragm and proximal gasket as disclosed herein.
Figure 2B:
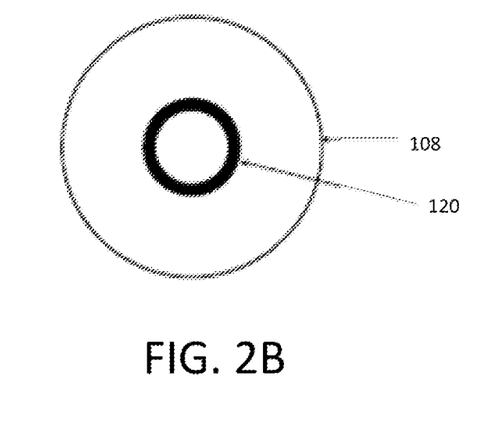
FIG. 2B is a top plan view of the diaphragm and proximal gasket of FIG. 2A.
Figure 3:
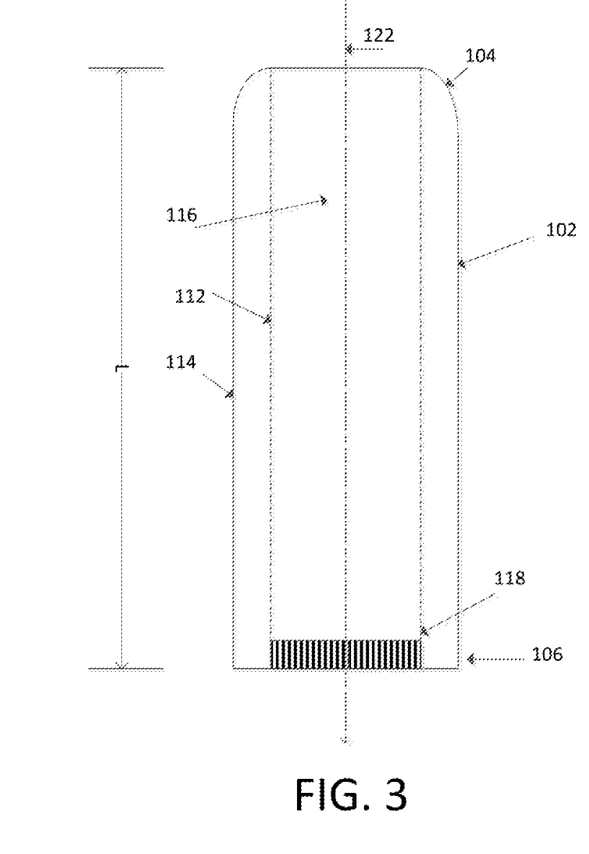
FIG. 3 is a cross-sectional view of an exemplary body and distal gasket as disclosed herein.
Figure 4:
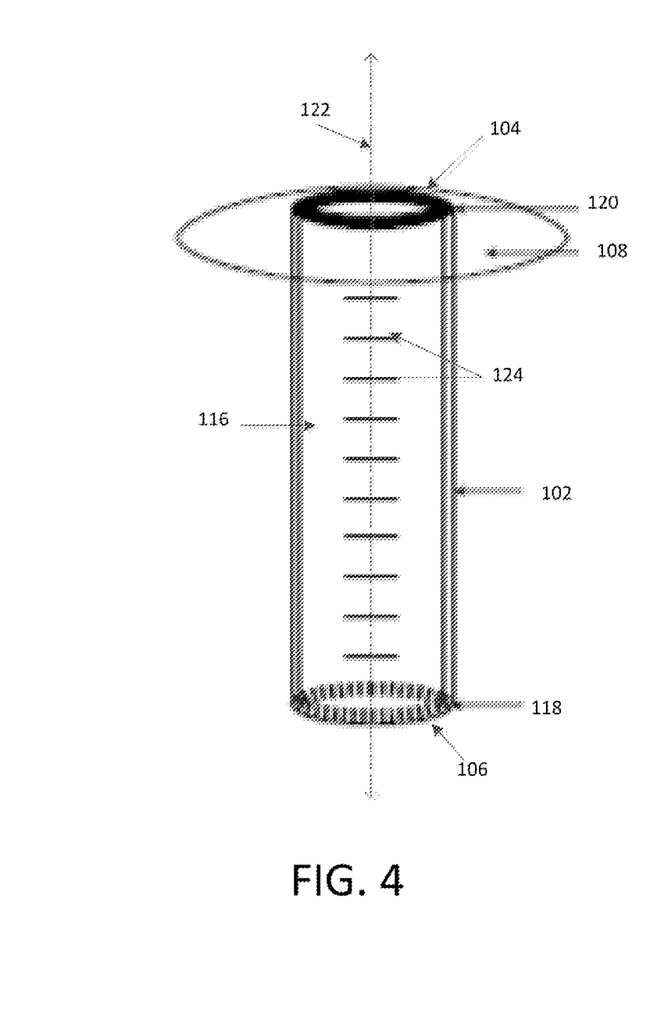
FIG. 4 is a partially transparent side perspective view of an exemplary device for maintaining air distension as disclosed herein.

As shown in FIGS. 1-8, a device 100 for preventing air escape and maintaining colonic air distension can comprise a body 102. Optionally, in exemplary aspects, the body 102 can have a substantially tubular shape with a round or circular cross-sectional shape. However, it is contemplated that other cross-sectional shapes can be used. In one aspect, and as shown in FIG. 1, the body 102 can have an inner surface 112 and an outer surface 114. The inner surface 112 and the outer surface 114 of the body 102 can be oriented along a longitudinal axis 122, and the body 102 can have a longitudinal length L relative to the longitudinal axis 122. The length L of the body 102 can be bounded by opposing proximal and distal ends 104, 106 of the body. In one aspect, the body 102 can have a length L that ranges from about 4 cm to about 15 cm, or from about 8 cm to about 12 cm, or from about 6 cm to about 10 cm, or from about 10 cm to about 15 cm. In a further aspect, the body 102 can have a length L that is less than 15 cm. In a further aspect, the body 102 can have a length L that is less than 12 cm. In another aspect, the body 102 can have a length L that is less than 10 cm. In another aspect, as depicted in FIG. 2, the outer surface of the proximal end 104 of the body 102 can be inwardly tapered in a proximal direction relative to the longitudinal axis 122. As shown in FIG. 3, in an aspect, the edges of the body 102 that define the proximal end 104 can be rounded so that no abrasive damage is caused to the colonoscope as the colonoscope exits the body 102 of the device. It is further contemplated that the rounded edges of the proximal end 104 can mitigate any damage to the sphincter during use of the device.

Figure 6:
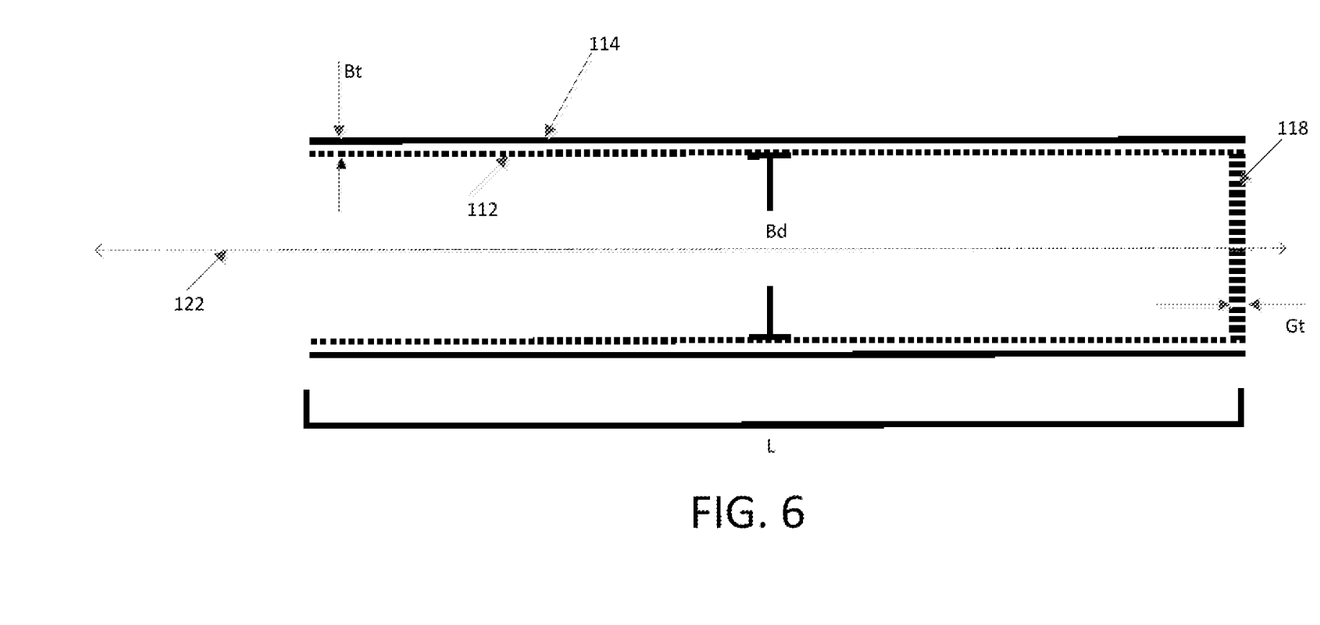
FIG. 6 is an isolated, cross-sectional side view of an exemplary body and distal gasket as disclosed herein.
Figure 8:
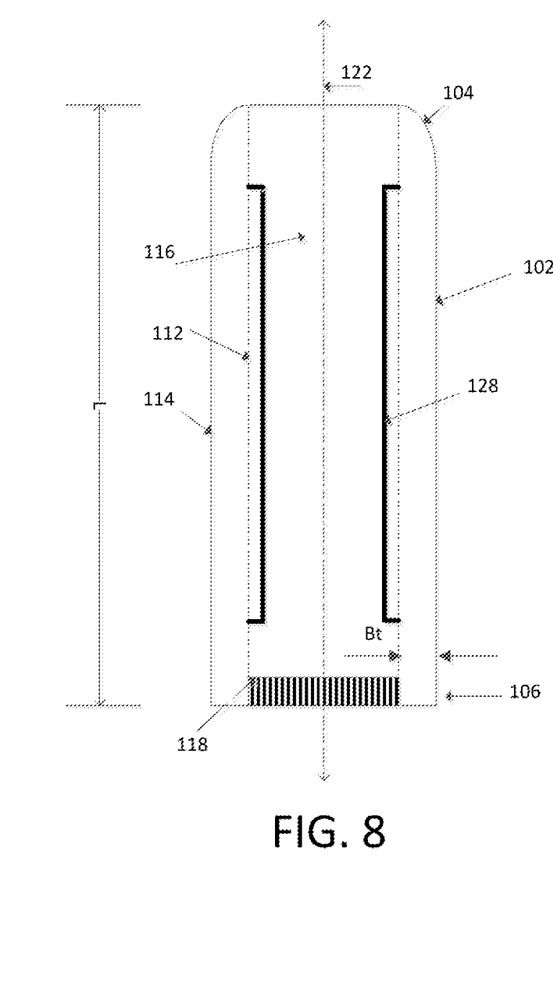
FIG. 8 is a cross-sectional view of an exemplary body with internal spine as disclosed herein.

As shown in FIG. 6, the body 102 can define a thickness Bt that represents a distance between the inner surface 112 and the outer surface 114 of the body 102. In exemplary aspects, the thickness of the body can range from about 0.5 mm to about 3 mm or from about 0.5 mm to about 1.5 mm and, optionally, be about 1 mm. As shown in FIG. 8, the body can be structurally reinforced with at least one internal spine 128 that projects radially inwardly from the inner surface 112 of the body 102. Optionally, as depicted in FIG. 8, the internal spine 128 can extend along (optionally, be oriented parallel or substantially parallel to) the longitudinal axis 122. Optionally, in other aspects, the internal spine 128 can be oriented perpendicular or substantially perpendicular to the longitudinal axis 122. Optionally, the internal spine can comprise a single internal spine, such as for example, a single internal spine that circumscribes the longitudinal axis 122. Optionally, the at least one internal spine 128 can comprise a plurality of internal spines 128 that can be spaced either axially or circumferentially relative to the longitudinal axis 122.

In another aspect, the inner surface 112 and the outer surface 114 of the body 102 can define a central bore 116. In this aspect, the central bore 116 can comprise a cavity that extends the length L of the body 102. In a further aspect, the central bore 116 can define a desired cross-sectional shape within a plane that is perpendicular to the longitudinal axis 122. Optionally, the desired cross-sectional shape can be a circle; however, it is contemplated that other cross-sectional shapes can be used. Regardless of the cross-sectional shape used, as shown in FIG. 6, it is contemplated that the central bore 116 can define a diameter Bd corresponding to a straight line extending between opposed points on the inner surface 112 of the body 102 and passing through a center point of the cross-sectional area of the body within a plane that is perpendicular to the longitudinal axis 122. Optionally, in exemplary aspects, the diameter of the central bore 116 can range from about 10 mm to about 20 mm or optionally, from about 12 mm to about 18 mm, including, for example and without limitation, diameters of about 12 mm, 13 mm, 14 mm, 15 mm, 16 mm, 17 mm, or 18 mm.

In another aspect, the outer surface 114 of the body can include at least one of marking (e.g., labeling) or texturing. The marking 124 can comprise graduations (e.g., graduated length markers) that can provide a relative indicator of the level of insertion of the colonoscope into the colon. For example, in exemplary aspects, the body 102 can comprise a partially transparent material with visible length markings. Thus, when the colonoscope traverses the central bore 116 of the body 102, the markings can provide an indication of the movement of the colonoscope 110. In another aspect, the outer surface can include texturing, such as ridges, stippling, grooves, indentations, a checkered pattern, bumps, scoring, or combinations thereof, which provides traction for an operator of the device. In use, it is contemplated that the texturing can provide additional dexterity to a colonoscope operator so that slippage can be mitigated.

Optionally, it is contemplated that the outer surface can comprise at least one projection (such as, for example, an axial ridge, a circumferential ridge, or bump) proximate a distal end of the body 102 that has an increased outer diameter relative to adjoining portions of the body. It is further contemplated that the at least one projection can define an outer diameter that is sufficient to prevent entrance of the at least one projection into the body of a subject, thereby ensuring that at least a portion of the body of the device remains outside the body of the subject. Optionally, it is contemplated that the at least one projection can project radially outwardly from the outer surface of the body by a distance of at least 3 mm. Thus, when a circumferential projection or a plurality of circumferentially spaced projections are provided, it is contemplated that the outer diameter of the body can be increased by at least 6 mm at the axial location where the at least one projection is positioned.

Optionally, in an exemplary aspect, the body 102 can comprise plastic. In use, it is contemplated that the plastic material can provide sufficient rigidity and dexterity for an operator of the device 100. Optionally, in further aspects, the body 102 can comprise a metallic material. In further aspects, the body 102 can comprise silicon. In other aspects, the body 102 can comprise an elastomer. It is contemplated that the body 102 can comprise any material or combination of materials that is biocompatible. In other aspects, it is contemplated that the body 102 can comprise of a combination of materials such that various physical parameters and usage-considerations, such as ease of sterilization or disposability, weight, durability and ease of dexterity for the operator.

In further aspects, and as shown in FIGS. 1, 3, and 6, the distal end 106 of the body 102 can comprise a distal gasket 118. In these aspects, the distal gasket 118 can be coupled to the distal end 106 of the body 102. In an exemplary aspect, the edges of the body 102 that define the distal end 106 can be rounded so that no abrasive damage is caused to the colonoscope as the body 102 of the device is advanced over the colonoscope. In a further aspect, the distal gasket 118 can define a central bore. The central bore of the distal gasket 118 can be positioned in fluid communication with the central bore 116 of the body. Thus, in use, as the device is advanced over the colonoscope (following initial positioning of a proximal portion of the colonoscope within the patient) in a proximal direction, the central bore of the distal gasket 118 can function as an orifice for more distal portions of the colonoscope 110 to traverse the distal gasket 118 and exit the central bore 116 of the body 102 (i.e., as the device moves in a proximal direction toward the subject, the device is axially advanced in the proximal direction over the length of the colonoscope such that an increased amount of the colonoscope is positioned distal to the distal gasket). It is contemplated that the distal gasket 118 can have a central axis (not shown) that is aligned with or at least generally oriented in the direction of the longitudinal axis 122 of the body 102. Thus, the distal gasket 118 can have a rim that is oriented perpendicularly or substantially perpendicularly relative to, and extends radially inwardly toward, the central axis (and the longitudinal axis 122). The central bore of the distal gasket 118 can also have a diameter that is less than the diameter of the central bore 116 of the body 102. It is contemplated that the difference between the diameter Bd of the central bore 116 of the body 102 and the diameter of the central bore of the distal gasket 118 (and proximal gasket 120 as further disclosed herein) can be selected to facilitate a stronger fit between the outer surface of a colonoscope 110 and the distal gasket and to reduce the ability for air to escape during a colonoscopy procedure or other procedure as disclosed herein, while still allowing for adequate movement of the body 102 relative to the colonoscope (and at least limited movement of the colonoscope relative to the body 102). In exemplary aspects, it is contemplated that the rim of the distal gasket 118 can have a radial thickness corresponding to the distance between (a) an inner surface of the distal gasket that defines the central bore of the distal gasket and (b) an outer surface that is spaced radially outwardly from the inner surface. Optionally, in these aspects, the radial thickness can range from about 2 mm to about 4 mm; however, it is contemplated that other dimensions can be used.

In exemplary aspects, and as shown in FIGS. 1-2B and 4-5B, the device 100 can further comprise a proximal gasket 120 that is coupled to the proximal end of the body 102. In an exemplary aspect, the edges of the body 102 that define the proximal end 104 can be rounded so that no abrasive damage is caused to the colonoscope during proximal advancement of the device over the colonoscope. The proximal gasket 120 can define a central bore that also has a central axis. The central bore of the proximal gasket 120 can be positioned in fluid communication with the central bore 116 of the body. Thus, in use, as the device is advanced over the colonoscope (following initial positioning of the proximal portion of the colonoscope within the patient), the central bore of the proximal gasket 120 can function as an orifice for a portion of the colonoscope 110 to traverse the proximal gasket 118 and enter the central bore 116 of the body 102 (i.e., as the device moves in a proximal direction toward the subject, the device is axially advanced in the proximal direction over the length of the colonoscope such that an increased amount of the colonoscope is positioned distal to the proximal gasket). The central axis of the proximal gasket 120 can be aligned with or at least generally oriented in the direction of the longitudinal axis 122. Thus, the proximal gasket 120 can have a rim that is oriented perpendicularly or substantially perpendicularly relative to, and extends radially inwardly toward, the central axis (and the longitudinal axis 122). In exemplary aspects, it is contemplated that the rim of the proximal gasket 120 can have a radial thickness corresponding to the distance between (a) an inner surface of the proximal gasket that defines the central bore of the proximal gasket and (b) an outer surface that is spaced radially outwardly from the inner surface. Optionally, in these aspects, the radial thickness can range from about 2 mm to about 4 mm; however, it is contemplated that other dimensions can be used.

Similar to the distal gasket 118, the central bore of the proximal gasket 120 can also have a diameter that is less than the diameter of the central bore of the body 102. In exemplary aspects, the central bores of the proximal gasket 120 and the distal gasket 118 can optionally have diameters ranging from about 8 mm to about 14 mm. However, it is contemplated that other diameters of the central bores of the proximal and distal gaskets 118, 120 can be used, provided the gaskets are capable of forming a fluid-tight seal with a colonoscope as further disclosed herein. As shown in FIG. 6, the proximal gasket 120 and the distal gasket 118 can each have a respective thickness Gt definable in the direction of the longitudinal axis 122 that ranges from about 0.5 mm to about 3 mm or from about 0.5 mm to about 1.5 mm and, optionally, is about 1 mm.

Figure 7:
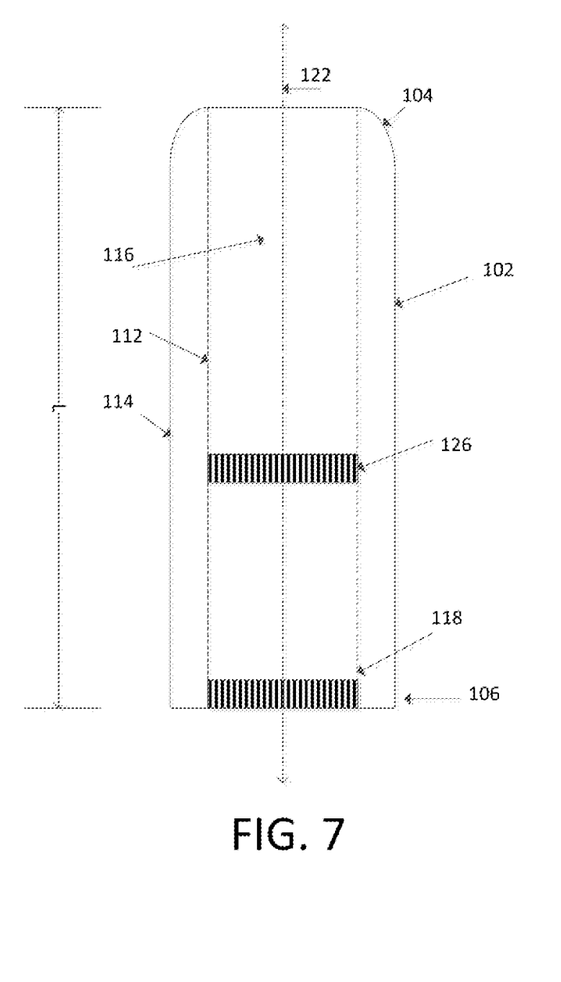
FIG. 7 is a cross-sectional view of an exemplary body, distal gasket, and internal gasket as disclosed herein.

In exemplary aspects, and as shown in FIG. 7, the device 100 can further comprise at least one internal gasket 126 that is coupled to the inner surface of the body 102 at an axial location between the proximal gasket and the distal gasket. It is contemplated that the internal gasket 126 can be placed at any point along the length of the body to further restrict or prevent air flow within the device. In a further aspect, when a single internal gasket 126 is provided, the internal gasket 126 can be located proximate a mid-point of the length of the body. In further exemplary aspects, it is contemplated that the at least one internal gasket 126 can comprise a plurality of internal gaskets that are axially spaced along the length of the body 102. Similar to the distal gasket 118 and the proximal gasket 120, each internal gasket 126 can define a central bore that also has a central axis. The central axis of the internal gasket 126 can be aligned with or at least generally oriented in the direction of the longitudinal axis 122. It is contemplated that the central bores of each internal gasket 126 can optionally have diameters ranging from about 8 mm to about 14 mm. However, it is contemplated that other diameters of the central bores of the internal gaskets 126 can be used, provided the gaskets are capable of forming a fluid-tight seal with a colonoscope as further disclosed herein.

In another aspect, the proximal gasket 120, the distal gasket 118, and the internal gasket 126 can comprise pliable materials. For example these materials can comprise silicone, rubber, neoprene, an elastomer, a pliable plastic material, or combination thereof. In exemplary aspects, the distal, proximal, and internal gaskets 118, 120, 126 can be secured to their respective portions of the body 102 using conventional medical-grade adhesive materials as are known in the art. In other aspects, it is contemplated that the distal and proximal gaskets can be configured for selective mechanical engagement with the distal and proximal ends of the body 102 such that the gaskets are selectively removable or detachable from the device for cleaning or replacement.

Figures 5A, 5B:
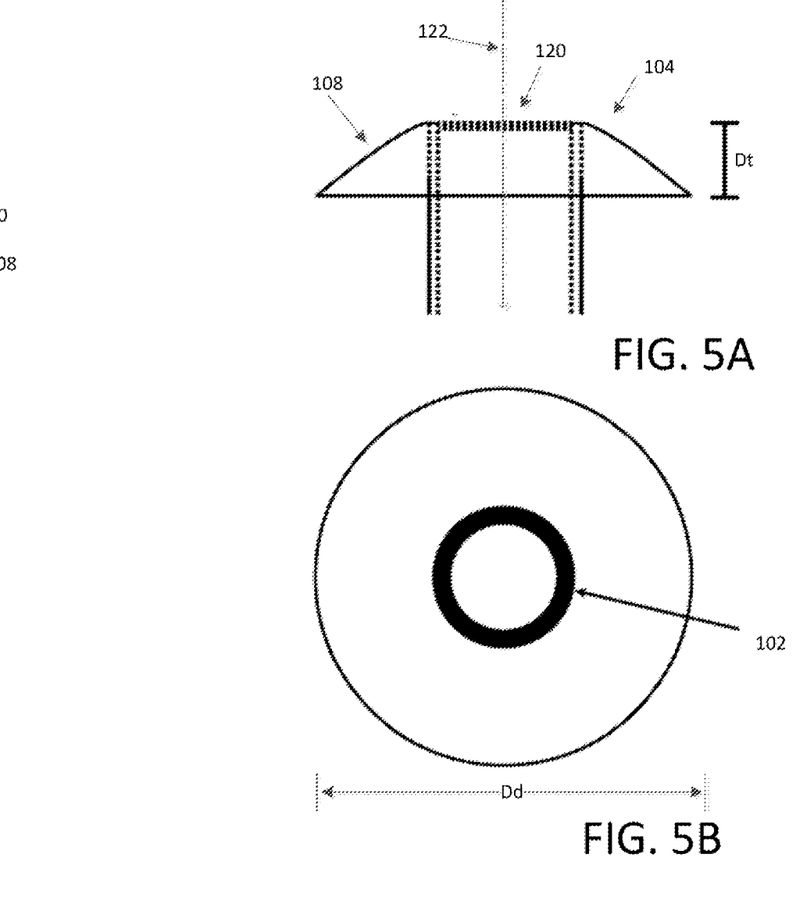
FIG. 5A is an isolated, partially transparent side view of an exemplary diaphragm, the proximal gasket, and the proximal end of the body as disclosed herein.
FIG. 5B is a top plan view of the diaphragm and the proximal gasket of FIG. 5A.

As shown in FIGS. 1-2B and 4-5B, a diaphragm 108 can be coupled to the proximal gasket 120. Optionally, in one aspect, the diaphragm 108 can circumscribe the proximal gasket 120. In circumscribing the proximal gasket, the diaphragm 108 can extend circumferentially around the proximal gasket 120 relative to the central axis of the proximal gasket 120 and the longitudinal axis 122 of the body 102. In further aspects, an inner surface of the diaphragm 108 can define a central bore that is configured to receive at least the proximal end of the body 102 such that the diaphragm circumferentially surrounds both the proximal gasket 120 and the proximal end of the body 102. In exemplary aspects, the inner surface of the diaphragm 108 can be secured to the outer surface of the body 102 by frictional engagement. Alternatively, in other exemplary aspects, the inner surface of the diaphragm 108 can be secured to the outer surface of the body using conventional medical-grade adhesives as are known in the art. Optionally, in another aspect and as shown in FIGS. 2A-2B, the proximal gasket 120 and the diaphragm 108 can comprise a unitary structure, which can optionally be formed as a single, monolithic piece. In this aspect, the proximal gasket 120 can be set into the diaphragm 108 such that the proximal gasket extends in a distal direction away from an outer surface of the diaphragm. As shown in FIG. 2A, the proximal gasket 120 can be oriented at an apex of diaphragm 108 extending in a proximal direction. In alternative aspects, and as shown in FIGS. 5A-5B, the distal gasket 120 and the diaphragm 108 can comprise distinct components that can comprise distinctly separate pieces that are configured for subsequent assembly. Optionally, in these aspects, the distal gasket can be configured for engagement with, or attachment to, the inner surface of the body, while the inner surface of the diaphragm can be configured for engagement with, or attachment to, the outer surface of the body. It is contemplated that such engagement or attachment can be through any conventional means, including for example and without limitation, mechanical engagement or adhesive attachment.

Optionally, as shown in FIGS. 1-2B and 4-5A, the diaphragm 108 can have an outer surface that defines a convex curvature. The convex curvature can be configured to increase the available surface area for forming a fluid-tight seal between the diaphragm and the sphincter muscle or other portion of the anus or stoma of the subject that is in contact with the diaphragm. In a further aspect, and as shown in FIG. 1, it is contemplated that the diaphragm can be inwardly tapered in a proximal direction (e.g., cone-shaped or substantially cone-shaped). Although described herein as having a convex curvature or a proximal taper, it is contemplated that the outer surface of the diaphragm can define any shape that is complementary to, and capable of forming a fluid-tight seal with, the anus or stoma of a subject. For example, in some optional aspects, it is contemplated that the diaphragm 108 can comprise a concave curvature or have a distal taper. As shown in FIG. 2A, for example, at least a portion of an underside of the diaphragm 108 can be inwardly tapered in a distal direction. It is contemplated that the distal taper can be configured to facilitate removal of the diaphragm from a rectum of the subject in the rare instance in which the diaphragm enters the rectum. In some optional aspects, it is contemplated that the outer surface or outer surfaces of the diaphragm 108 can define both a proximal and a distal taper along respective portions of the longitudinal (axial) length of the diaphragm. In addition to a distal taper, it is contemplated that the diaphragm 108 can further comprise a distal end portion (positioned distal to the distally tapered portion) that can optionally be configured for complementary engagement with (e.g., receipt within or receipt of) or coupling to a proximal end of the body of the device).

In exemplary aspects, the diaphragm 108 can have a longitudinal length or thickness Dt, along the direction of the longitudinal axis 122, ranging from about 3 mm to about 30 mm, from about 4 mm to about 10 mm, from about 5 mm to about 7 mm, or from about 5 mm to about 15 mm. In yet another aspect, the diaphragm 108 can have a maximum outer diameter Dd ranging from about 2 cm to about 6 cm or from about 2.5 cm to about 4 cm. In order to facilitate a fluid tight interface with the anus of the subject, the diaphragm 108 can comprise one or more pliable materials. For example, these materials can comprise silicone, rubber, neoprene, an elastomer, a pliable plastic material or combination thereof.

Optionally, in exemplary aspects, it is contemplated that the body 102 and the components of device within or coupled to the body 102, can be provided as a one-piece, unitary structure. Optionally, in these aspects, it is contemplated that the body 102, the gaskets 118, 120 (and 126, where provided), the diaphragm 108, and any internal spine 128 can be provided as a one-piece, unitary structure, which in exemplary aspects, can be produced as a single piece using a conventional three-dimensional (3D) printing process.

Also shown in FIG. 1 is a colonoscope 110, which can be a tubular device that can be inserted through the body 102 during a colonoscopy or other procedure requiring access to a subject or patient as is known in the art. After advancing a proximal portion of the colonoscope 110 through the anus of the subject, the body 102 of the device 100 can be advanced over the portion of the colonoscope outside the subject such that a distal end of the colonoscope 110 axially passes through the central bores of the proximal gasket 120 and the body 102 and then traverses the central bore of the distal gasket 118 to exit the device. As the body 102 of the device 100 is advanced over the colonoscope, the proximal and distal gaskets can form a fluid-tight seal with the colonoscope. After the device 100 is advanced over the colonoscope, the device can be further advanced in a proximal direction to a desired use position in which the diaphragm of the device can form a fluid-tight seal with at least one of the anus and the stoma of the subject. In use, the device can slide relative to the colonoscope as needed to selectively seal air within the subject and to selectively release air from the subject. Thus, this process can be instantaneously and selectively reversed by sliding the device away (in a distal direction) 1-2 mm to allow for an immediate release of air from the subject. Conversely, the device can also be readily available by a sliding movement (in a proximal direction) to return to the subject's orifice to provide the benefit of maintaining the air within the lumen temporarily and therefore achieving procedural goals, intermittently throughout the procedure. Although selective sliding movement of the device is possible, it is also contemplated that the device can remain static when in contact with the anus or the stoma of the subject, with minor adjustments of the position of the colonoscope being the only movement/adjustment required during the procedure. With the device 100 operatively positioned over portions of the colonoscope, the colonoscope can be used to examine the colon (not shown). During a colonoscopy or other procedure in which the colonoscope is advanced within the colon or small bowel of a subject, the colonoscope 110 can be used in the conventional manner to provide a visual representation of the colon, small bowel, and other regions accessed by the colonoscope. In exemplary aspects, the colonoscope can be an adult-size colonoscope having a diameter ranging from about 12.8 mm to about 13.2 mm. In other exemplary aspects, the colonoscope can be a pediatric-size colonoscope having a diameter ranging from about 11.5 mm to about 11.7 mm. However, it is contemplated that any size of colonoscope can be used with the device 100 disclosed herein, and it is further contemplated that the operative diameters and dimensions of the disclosed device 100 can be selected as appropriate to ensure formation of a fluid-tight seal with the colonoscope.

In one aspect of the embodiment, the colonoscope 110 and the device 100 can function as a system for performing medical procedures as disclosed herein. Optionally, it is contemplated that the components of the device 100 can be provided along with the colonoscope as a kit. For example, in exemplary aspects, it is contemplated that a conventional colonoscope can be packaged with a device 100 for maintaining air distension as disclosed herein, with the device and the colonoscope of the package having a complementary size and shape such that a clinician can know the device is compatible with the colonoscope. In a further aspect, the device 100 can further comprise a coupling element that is configured to permit selective engagement between the device 100 and the colonoscope 110. During use, the coupling element can be configured to mechanically engage a portion of the colonoscope to prevent or limit movement of the device 100, thereby aiding the device in maintaining an air-tight seal during a medical procedure as disclosed herein. In exemplary aspects, the coupling element can comprise a strap. In other exemplary aspects, the coupling element can comprise a clamp. However, more generally, it is contemplated that any conventional coupling or temporary fastening mechanism can be used. Optionally, in some aspects, the coupling element can be permanently secured to a portion of the outer surface of the body 102 of the device 100. In further optional aspects, it is contemplated that the colonoscope 110 can be provided with a ring that circumferentially surrounds a portion of the colonoscope and defines an engagement element (a projection, a hook, a loop, a tether, and the like) that is configured to be engaged by the coupling element of the device 100.

A method for using the device 100 can include advancing a colonoscope through at least one of an anus and a stoma of a subject. In another aspect, the method can comprise advancing a device 100 as disclosed herein over portions of the colonoscope 110 outside the subject such that portions of the colonoscope pass through the central bores of the proximal gasket 120, the body 102, and the distal gasket 118 of the device, with a distal end of the colonoscope protruding from the distal gasket (in a distal direction). In this aspect, the distal gasket 118 and the proximal gasket 120 can form a fluid tight seal with the outer surface of the colonoscope 110. In a further aspect, the method can comprise positioning the diaphragm of the device in contact with at least one of the anus and the stoma of the subject. In exemplary aspects, it is contemplated that the diaphragm can form a fluid-tight seal with at least one of the anus and the stoma of the subject, thereby ensuring that air distension within the subject is maintained.

In exemplary applications, it is contemplated that this process can be selectively and/or instantaneously reversed by sliding the device away from the subject (in a distal direction) by a selected distance (e.g., 1-2 mm) to break the seal between the diaphragm and the orifice of the subject and to allow immediate air release from the subject. Conversely, it is further contemplated that the device can be selectively moved in a proximal direction to again engage the subject and form a fluid-tight seal, thereby providing the benefit of maintaining the air within the lumen temporarily and allowing for the achievement of procedural goals, intermittently throughout the procedure. Thus, in operation, it is contemplated that the disclosed device can be configured for selective sliding movement relative to the colonoscope to thereby selectively seal air within the subject and to selectively release air from the subject. It is further contemplated that such flexibility in the movement of the device can ensure that the device is safely applied as necessary to maintain air distension while also providing for fast and easy removal of the device from engagement with the subject to prevent undesired injury to the subject.

In exemplary aspects, the disclosed device 100 can be used in the performance of a conventional colonoscopy procedure. However, in other exemplary aspects, the disclosed device 100 can be used to maintain colon distension in the performance of colostomy evaluations as are known in the art. In still other exemplary aspects, it is contemplated that the disclosed device 100 can be used to maintain small bowel distension in the performance of ileostomy evaluations as are known in the art.

Optionally, in exemplary aspects, it is contemplated that the disclosed device can be provided as a disposable device, such as, for example and without limitation, a device that is intended for a single use. Alternatively, in other exemplary aspects, it is contemplated that the disclosed device can be configured for repeated uses, with the various components of the device (e.g., the diaphragm, the proximal and distal gaskets, and the body) being configured for selective cleaning and sterilization in between procedures.

Optionally, in further exemplary aspects, it is contemplated that the outer surface of the body of the disclosed device can have a surface roughness that exceeds that of the diaphragm.

Exemplary Aspects

In view of the described devices, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A device for maintaining colonic air distension, comprising: a body having a longitudinal axis, an inner surface, an outer surface, a proximal end, and an opposed distal end spaced from the proximal end relative to the longitudinal axis, wherein the inner surface of the body defines a central bore surrounding the longitudinal axis and extending from the proximal end to the distal end of the body, wherein the central bore has a diameter; a distal gasket coupled to the distal end of the body, wherein the distal gasket defines a central bore and has a central axis that is aligned with the longitudinal axis of the body, wherein the central bore of the distal gasket has a diameter that is less than the diameter of the central bore of the body; a proximal gasket coupled to the proximal end of the body, wherein the proximal gasket defines a central bore and has a central axis that is aligned with the longitudinal axis of the body, wherein the central bore of the proximal gasket has a diameter that is less than the diameter of the central bore of the body; and a diaphragm coupled to the proximal gasket, wherein the diaphragm extends radially outwardly from the proximal gasket relative to the central axis of the proximal gasket and the longitudinal axis of the body, wherein the distal and proximal gaskets are configured to form a fluid-tight seal with a colonoscope positioned within the central bores of the distal gasket, the body, and the proximal gasket, and wherein the diaphragm is shaped to conform to at least one of an anus and a stoma of a subject.

Aspect 2: The device of aspect 1, wherein the proximal gasket and the diaphragm comprise a unitary structure.

Aspect 3: The device of aspect 1 or aspect 2, wherein the body is substantially tubular.

Aspect 4: The device of any one of aspects 1-3, wherein the body has a longitudinal length that is less than 15 cm.

Aspect 5: The device of any one of aspects 1-3, wherein the body has a longitudinal length that is less than 10 cm.

Aspect 6: The device of any one of aspects 1-3, wherein the body has a longitudinal length ranging from about 4 cm to about 15 cm.

Aspect 7: The device of any one of the preceding aspects, wherein at least a portion of the outer surface of the body is scored.

Aspect 8: The device of any one of the preceding aspects, wherein at least a portion of the outer surface of the body is grooved.

Aspect 9: The device of any one of the preceding aspects, wherein the diaphragm has an outer diameter that decreases moving in a proximal direction toward the proximal gasket.

Aspect 10: The device of any one of the preceding aspects, wherein the diaphragm has an outer surface with a convex curvature.

Aspect 11: The device of any one of aspects 1-9, wherein the diaphragm is inwardly tapered in at least one of a proximal direction and a distal direction.

Aspect 12: The device of any one of the preceding aspects, wherein the outer surface of the proximal end of the body is inwardly tapered in a proximal direction.

Aspect 13: The device of any one of the preceding aspects, wherein the diaphragm has a longitudinal length ranging from about 5 mm to about 30 mm.

Aspect 14: The device of any one of the preceding aspects, wherein the diaphragm has a maximum outer diameter ranging from about 2 cm to about 6 cm.

Aspect 15: The device of any one of the preceding aspects, wherein the central bore of the body has a diameter ranging from about 12 mm to about 18 mm.

Aspect 16: The device of any one of the preceding aspects, wherein the central bores of the proximal and distal gaskets have diameters ranging from about 8 mm to about 14 mm.

Aspect 17: The device of any one of the preceding aspects, wherein the body comprises plastic, silicon, or an elastomer.

Aspect 18: The device of any one of the preceding aspects, wherein the proximal and distal gaskets and the diaphragm comprise a pliable material.

Aspect 19: The device of aspect 18, wherein the pliable material is silicone, neoprene, or an elastomer.

Aspect 20: The device of claim 1, further comprising at least one spine extending along the longitudinal axis of the body configured to provide structural support to the body.

Aspect 21: The device of claim 1, further comprising at least one internal gasket coupled to the inner surface of the body at an axial location between the proximal gasket and the distal gasket, wherein the at least one internal gasket is configured to restrict air flow within the device.

Aspect 22: A colonoscopy system comprising: a device of any one of the preceding claims; and a colonoscope.

Aspect 23: The colonoscopy system of aspect 22, wherein the colonoscope has an outer diameter ranging from about 12 mm to about 14 mm.

Aspect 24: The colonoscopy system of aspect 22, wherein the colonoscope has an outer diameter ranging from about 11 mm to about 12 mm.

Aspect 25: A colonoscopy method comprising: positioning the diaphragm of a device of any one of aspects 1-21 in contact with at least one of an anus and a stoma of a subject; advancing a colonoscope through the central bores of the distal gasket, the body, and the proximal gasket of the device such that a distal end of the colonoscope protrudes from the proximal gasket, wherein the distal and proximal gaskets form a fluid-tight seal with the colonoscope; and advancing the colonoscope through the anus of the subject.

Aspect 26: The colonoscopy method of aspect 25, wherein the diaphragm forms a fluid-tight seal with at least one of the anus and the stoma of the subject.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A method comprising:
    advancing a device over a distal portion of a colonoscope, the distal portion of the colonoscope being positioned outside a body of a subject, wherein an opposing proximal portion of the colonoscope is positioned within the subject through at least one of an anus or a stoma of the subject, wherein a body of the device has a longitudinal axis, an inner surface, an outer surface, a proximal end, and an opposed distal end, wherein the body defines a central bore surrounding the longitudinal axis, wherein the central bore has a diameter, wherein the device further comprises:
        at least one gasket coupled to the body of the device, wherein each gasket of the at least one gasket defines a central bore, wherein the central bore of each gasket of the at least one gasket has a diameter that is less than the diameter of the central bore of the body of the device, wherein the device is advanced over the distal portion of the colonoscope such that portions of the colonoscope pass through the central bores of each gasket of the at least one gasket and the body and a distal end of the colonoscope protrudes from the distal end of the body, wherein the at least one gasket forms a fluid-tight seal with an outer surface of the colonoscope; and
        a sealing element coupled to the proximal end of the body of the device and extending radially outwardly beyond the outer surface of the body of the device;
    further advancing the device over the colonoscope in a proximal direction toward the subject such that the sealing element of the device forms a fluid-tight seal with the at least one of the anus or the stoma of the subject;
    moving the device away from the subject in a distal direction to break the seal between the sealing element and the at least one of the anus or the stoma of the subject to allow immediate air release from the subject; and
    moving the device in a proximal direction to again engage the subject and form a fluid-tight seal between the sealing element and the at least one of the anus or the stoma of the subject,
    wherein the entire body of the device remains outside the body of the subject.

2. The method of claim 1, wherein the at least one gasket comprises a distal gasket coupled to the distal end of the body.

3. The method of claim 1, wherein the body is substantially tubular.

4. The method of claim 1, wherein the body has a longitudinal length ranging from about 4 cm to about 15 cm.

5. The method of claim 1, wherein at least a portion of the outer surface of the body is scored or grooved.

6. The method of claim 1, wherein the sealing element has an outer diameter that decreases moving in a proximal direction.

7. The method of claim 6, wherein the sealing element has an outer surface with a convex curvature.

8. The method of claim 6, wherein at least a portion of an underside of the sealing element is inwardly tapered in a distal direction.

9. The method of claim 6, wherein the sealing element has a longitudinal length of at least 5 mm.

10. The method of claim 6, wherein the sealing element has a maximum outer diameter ranging from about 2 cm to about 6 cm.

11. The method of claim 1, wherein the central bore of the body has a diameter ranging from about 12 mm to about 18 mm.

12. The method of claim 11, wherein the central bore of each gasket of the at least one gasket has a diameter ranging from about 8 mm to about 14 mm.

13. The method of claim 1, wherein the at least one gasket comprises a pliable material.

14. The method of claim 1, further comprising at least one spine extending along the longitudinal axis of the body and configured to provide structural support to the body.

15. The method of claim 2, further comprising a proximal gasket coupled to the proximal end of the body.

16. The method of claim 15, further comprising at least one internal gasket coupled to the inner surface of the body between the distal and proximal gaskets, wherein the at least one internal gasket is configured to restrict air flow within the device.

17. The method of claim 15, wherein the proximal gasket and the sealing element comprise a unitary structure.

18. The method of claim 1, wherein the method is performed during a colonoscopy procedure, wherein the proximal portion of the colonoscope is positioned within the subject through the anus of the subject, wherein the fluid-tight seal is formed between the sealing element and the anus of the subject.

19. The method of claim 1, wherein the method is performed during a colostomy or ileostomy evaluation, wherein the proximal portion of the colonoscope is positioned within the subject through the stoma of the subject, and wherein the fluid-tight seal is formed between the sealing element and the stoma of the subject.

20. The method of claim 1, wherein the sealing element comprises a diaphragm.

* * * * *